United States Patent [19]

Taylor et al.

[11] Patent Number: 5,484,433
[45] Date of Patent: Jan. 16, 1996

[54] TISSUE ABLATING DEVICE HAVING A DEFLECTABLE ABLATION AREA AND METHOD OF USING SAME

[75] Inventors: Kevin D. Taylor; Dan J. Hammersmark, both of Colorado Springs, Colo.; Timothy J. Wood, Santa Clara, Calif.

[73] Assignee: The Spectranetics Corporation, Colorado Springs, Colo.

[21] Appl. No.: 177,095

[22] Filed: Dec. 30, 1993

[51] Int. Cl.⁶ ............................................. A61N 5/06
[52] U.S. Cl. ..................... 606/17; 606/7; 606/10; 606/15
[58] Field of Search ................................ 606/2–18

[56] References Cited

U.S. PATENT DOCUMENTS

| | | | |
|---|---|---|---|
| 4,240,431 | 12/1980 | Komiya | 606/15 |
| 4,686,979 | 8/1987 | Gruen et al. | 128/303.1 |
| 4,718,417 | 1/1988 | Kittrell et al. | 606/16 |
| 4,771,777 | 9/1988 | Horzewski et al. | 128/344 |
| 4,781,681 | 11/1988 | Sharrow et al. | 604/96 |
| 4,784,132 | 11/1988 | Fox et al. | 128/303.1 |
| 4,790,310 | 12/1988 | Ginsburg et al. | 128/303.1 |
| 4,790,315 | 12/1988 | Mueller, Jr. et al. | 128/344 |
| 4,799,479 | 1/1989 | Spears | 606/7 |
| 4,800,876 | 1/1989 | Fox et al. | 128/303.1 |
| 4,848,336 | 7/1989 | Fox et al. | 606/7 |
| 4,875,897 | 10/1989 | Lee | 604/283 |
| 4,906,230 | 3/1990 | Maloney et al. | 604/95 |
| 4,966,596 | 10/1990 | Kuntz et al. | 606/7 |
| 5,029,588 | 7/1991 | Yock et al. | 128/662.06 |
| 5,041,108 | 8/1991 | Fox et al. | 606/7 |
| 5,066,292 | 11/1991 | Müller et al. | 606/7 |
| 5,114,403 | 5/1992 | Clarke et al. | 604/96 |
| 5,123,421 | 6/1992 | Sinofsky | 128/772 |
| 5,133,725 | 7/1992 | Quadri | 606/159 |
| 5,176,674 | 1/1993 | Hofmann | 606/7 |
| 5,188,111 | 2/1993 | Yates et al. | 128/657 |
| 5,188,632 | 2/1993 | Goldenberg | 606/7 |
| 5,196,024 | 3/1993 | Barath | 606/159 |
| 5,199,950 | 4/1993 | Schmitt et al. | 604/95 |
| 5,203,772 | 4/1993 | Hammerslag et al. | 604/95 |
| 5,217,454 | 6/1993 | Khoury | 606/7 |

*Primary Examiner*—David M. Shay
*Attorney, Agent, or Firm*—Cushman, Darby & Cushman

[57] ABSTRACT

An apparatus for ablating biological tissue having a deflectable ablation area including an elongated catheter having a distal end, a proximal end, and an elongated body portion. A plurality of optical fibers extend between the proximal and distal ends of the catheter. The distal ends of all of the plurality of optical fibers define an ablation area at the distal end of the catheter. The catheter includes a device for selectively deflecting the distal ends of all of the optical fibers so that at least a portion of the ablation area extends beyond an area defined by the cross-sectional area of the catheter while the amount of light energy over the entire ablation area remains constant.

19 Claims, 7 Drawing Sheets

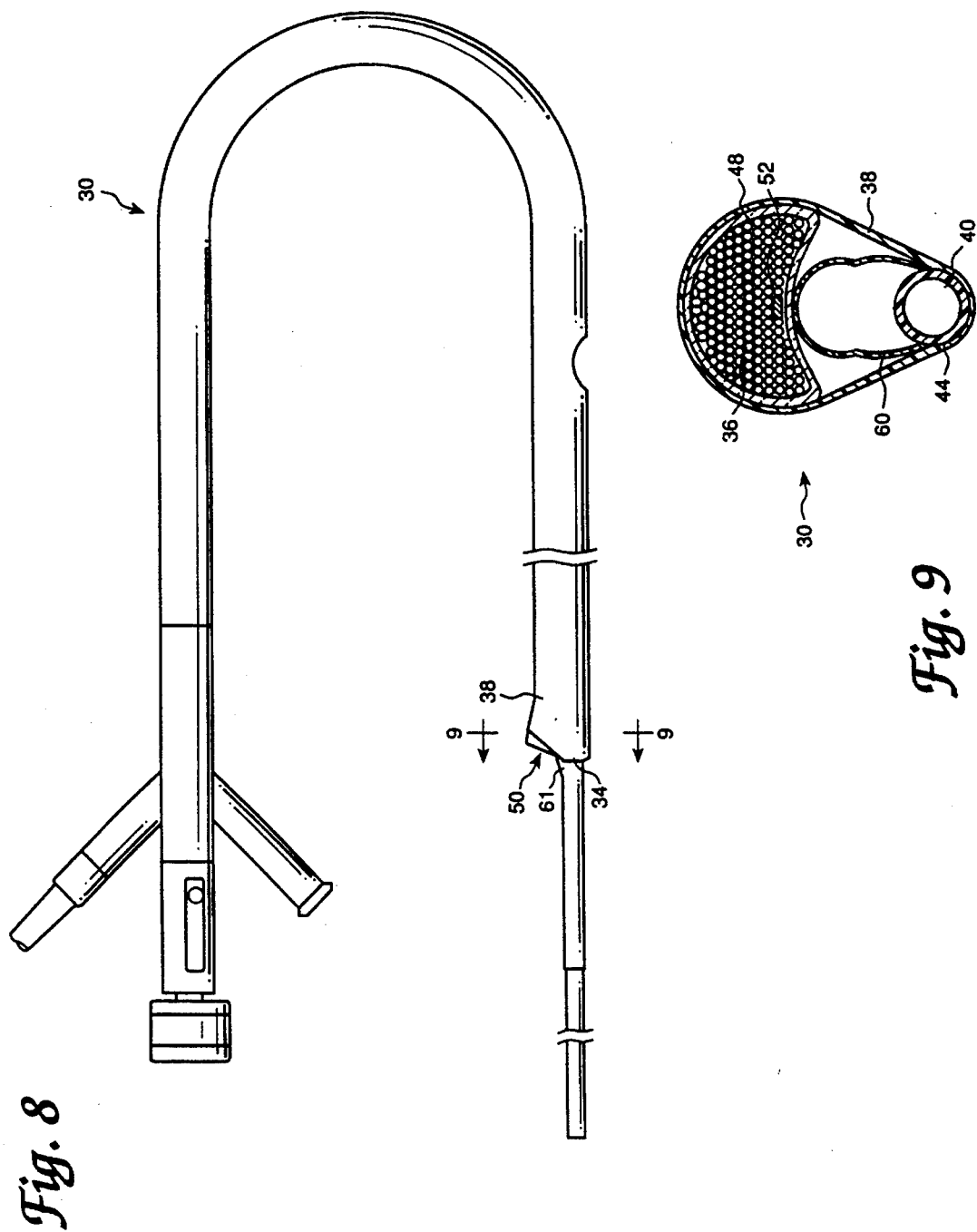

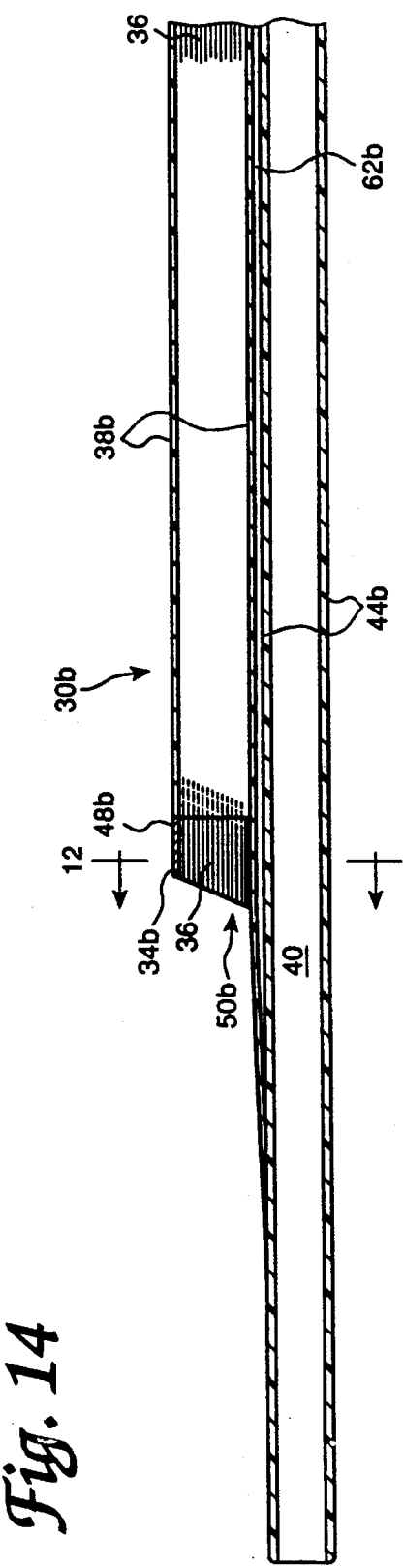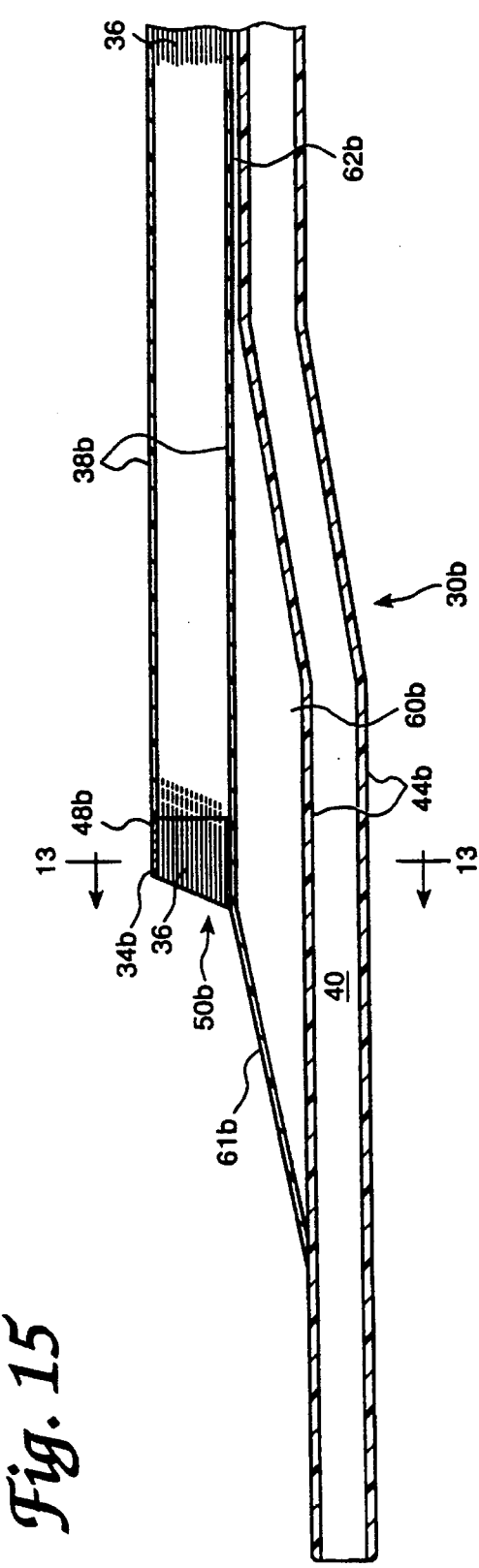

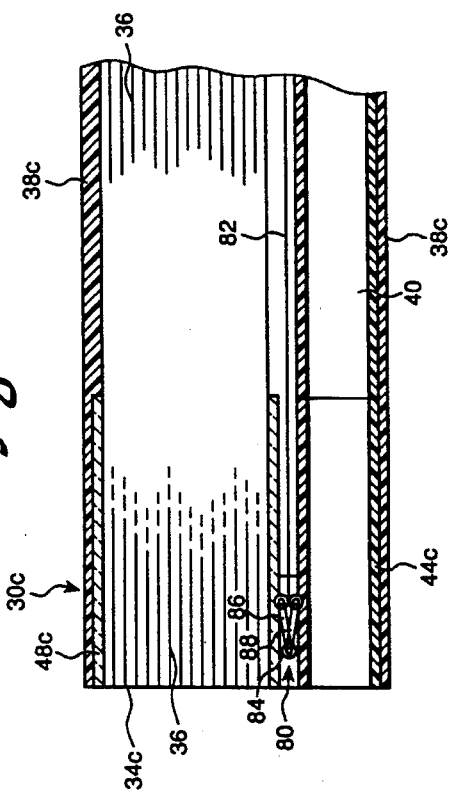
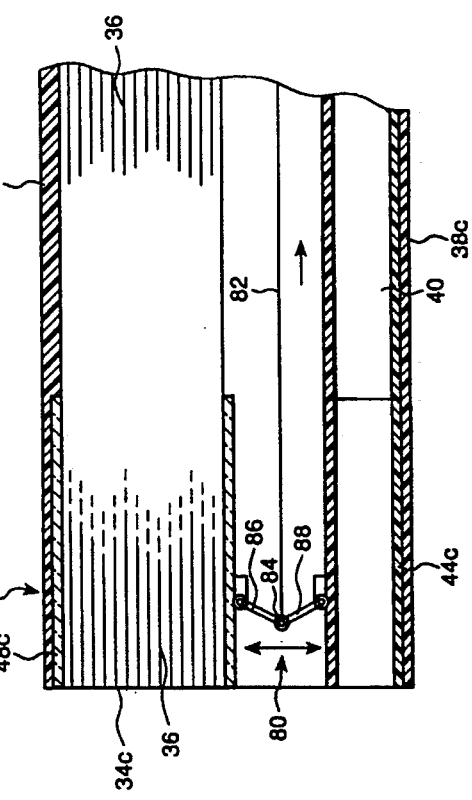
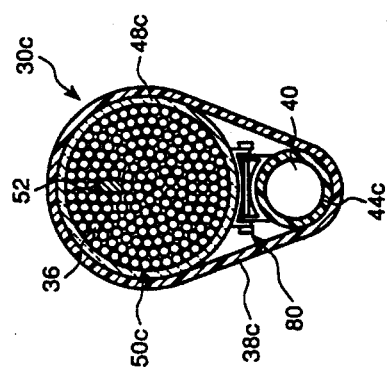
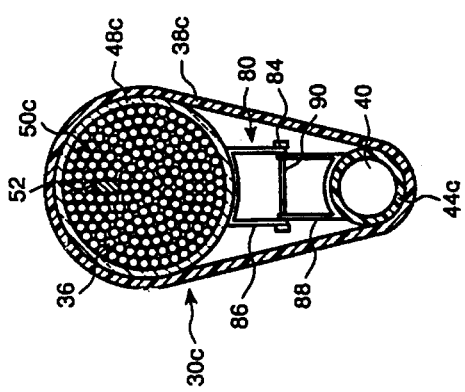

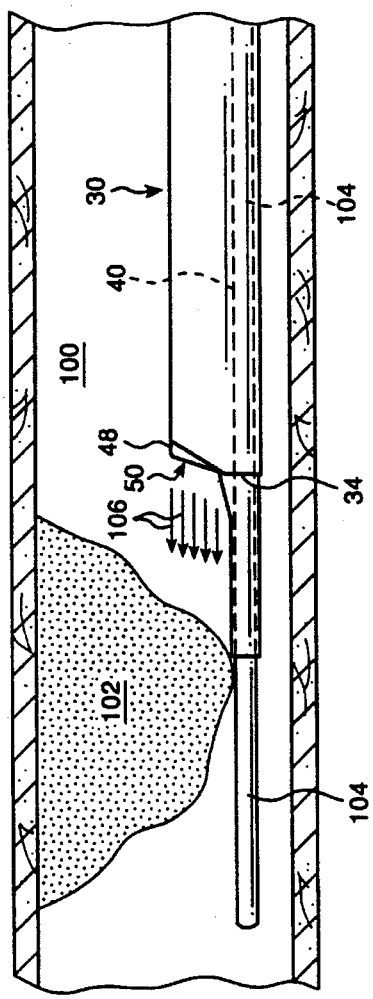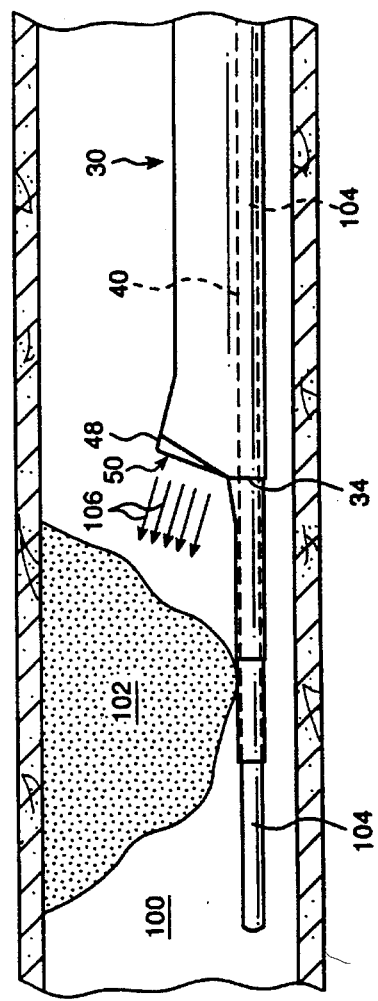

TISSUE ABLATING DEVICE HAVING A DEFLECTABLE ABLATION AREA AND METHOD OF USING SAME

BACKGROUND OF THE INVENTION

1. Field of the Invention

The present invention relates to an apparatus and method for ablating biological tissue. In particular, the present invention relates to a catheter and a method of using a catheter including a bundle of optical fibers defining an ablation area at the distal end thereof. The entire bundle of optical fibers at the distal end of the catheter is deflectable with respect to a guidewire lumen so that a constant fluence is maintained over the ablation area.

2. Description of the Related Art

Numerous devices are known for using light energy to ablate an obstruction, such as plaque and thrombus, in a patient's body cavities or vessels. For example, U.S. Pat. No. 4,686,979 to Gruen; U.S. Pat. No. 5,188,632 to Goldenberg; and U.S. Pat. No. 5,041,108 to Fox et al. each disclose a laser catheter for ablating tissue in a body. In these devices, light energy is emitted from the distal end of the catheter by a plurality of optical fibers extending therethrough. The distal ends of the optical fibers define an ablation area, which is an area where tissue is ablated by the light energy emitted from the optical fibers. The amount of light energy emitted by the optical fibers per unit area is referred to as the fluence. To ablate obstructions in a cavity or vessel, it can be appreciated that catheters having small diameters are preferred because they can be inserted through smaller blood vessels and are less cumbersome to manipulate.

It is also known to deflect the distal ends of the optical fibers away from the path of the catheter so that the light energy emitted from the distal end of the fibers can be aimed at the tissue to be ablated. A common method for deflecting the distal ends of the optical fibers is to deflect the entire distal end of the catheter. For example, U.S. Pat. No. 5,188,632 to Goldenberg; U.S. Pat. No. 5,111,403 to Clarke et al.; U.S. Pat. No. 5,029,588 to Yock et al.; and U.S. Pat. No. 4,966,596 to Kuntz et al. each disclose a laser catheter having at least one inflatable balloon at or near the exterior surface at the distal end of the catheter. Inflating the balloon within a blood vessel, for example, forces the balloon against the wall of the vessel thereby moving the entire distal end of the catheter—including a guidewire and/or guidewire lumen located therein—within the blood vessel. However, this method of deflecting the ablation area works against the course of the guidewire, thereby inhibiting the ability of the catheter to continue to be inserted and/or manipulated while the balloon is inflated. Additionally, this deflecting method does not permit the distal ends of the optical fibers to be aimed outside the diameter of the distal end of the catheter.

U.S. Pat. No. 5,176,674 to Hoffman and U.S. Pat. No. 4,790,310 to Ginsburg each disclose a laser catheter wherein the distal ends of the optical fibers are deflectable beyond the diameter of the catheter. Therefore, these devices enable light energy to be selectively directed over an area that is larger than the diameter at the distal end of the catheter, thereby increasing the size of the cut made by the catheter. In these devices, however, the fluence over the ablation area does not remain constant as the distal ends of the optical fibers are deflected. This is because the optical fibers in the bundle of fibers at the distal end of the catheter spread apart from one another during deflection, thus increasing the size of the ablation area while the magnitude of the light energy remains constant.

U.S. Pat. Nos. 5,941,108; 4,800,876; and 4,784,132 to Fox and U.S. Pat. No. 4,875,897 to Lee disclose a catheter having a bundle of optical fibers that are deflectable at the distal end such that the fluence remains constant. In these devices, the bundle of optical fibers at the distal end of the catheter are shifted by at least one balloon positioned between the optical fibers and the wall of the catheter. However, the bundle of fibers can only be moved within an area defined by the cross-sectional area of the distal end of the catheter when the balloon is not expanded. That is, the ablation area cannot be deflected outside the diameter of the catheter. Therefore, in order to ablate a large obstruction, a catheter having a relatively large diameter and/or an inflatable balloon at the exterior of the catheter to move the catheter within the vessel is necessary.

U.S. Pat. No. 5,066,292 to Muller discloses a laser catheter having three distinct groups of optical fibers. Each group of optical fibers defines an ablation area at the distal end of the catheter. The three groups of optical fibers are concentrically located at the distal end of the catheter and separated from one another by an elastic intermediate zone. Each of the three groups of optical fibers are deflectable beyond the diameter of the catheter by inflating a balloon centrally located within the catheter, which, when inflated, causes the elastic intermediate zones between the groups of optical fibers to expand. The individual optical fibers in each group of optical fibers are rigidly connected to one another so that the fluence over the ablation area defined by each group of optical fibers does not decrease during deflection. However, because the three separate bundles of optical fiber spread apart from one another, the fluence over the entire ablation area at the distal end of the catheter does not remain constant during deflection.

Muller also discloses cutting off the light energy from two of the three groups of optical fibers so that only one group of optical fibers is used to ablate the tissue. Doing so, however, results in an inefficient use of the limited space within a blood vessel by the catheter. As discussed above, it is desirable that vascular catheters have as small a diameter as possible. When only one ablation area is used in the Muller device, the remaining portions of the catheter, including the two unused groups of optical fibers serve no purpose, thereby unnecessarily increasing the diameter of the catheter so that the catheter is unable to pass through small vessels.

SUMMARY OF THE INVENTION

It is, therefore, an object of the present invention to provide an apparatus for ablating biological tissue that overcomes the problems associated with the above-identified laser catheter devices. In accordance with the principles of the present invention, this object is achieved by providing an elongated catheter having an elongated body portion and a plurality of optical fibers extending from a proximal end to a distal end of the catheter. The distal ends of the plurality of optical fibers define an ablation area at the distal end of the catheter. The catheter includes a deflecting device for selectively deflecting the distal ends optical fibers at the distal end of the catheter such that the fluence over the entire ablation area at the distal end of the catheter remains constant whether or not the deflecting device is actuated and at least a portion of the ablation area is deflected beyond an area defined by the cross-sectional area of the catheter at the distal end thereof when the deflecting device is not actuated.

It is a further object of the present invention to provide a catheter having a deflectable ablating area that is simple in construction, economical in manufacture, and effective in operation.

Other objects, features, and characteristics of the present invention as well as the methods of operations and functions of the related elements of structure, and the combination of parts and economies of manufactures, will become more apparent upon consideration of the following description and the appended claims with reference to the accompanying drawings, all of which form a part of the specification, wherein like numerals designate corresponding parts in the various figures.

BRIEF DESCRIPTION OF THE DRAWINGS

FIG. 8 is a side view of the ablation device of FIG. 1 showing the ablation area in a deflected position;

FIG. 9 is a cross-sectional view taken along line 9—9 of FIG. 8;

FIG. 14 is a fragmented side sectional view of the distal end of the ablation device shown in FIG. 12;

FIG. 15 is a fragmented side section view of the distal end of the ablation device shown in FIG. 13;

FIG. 16 is an end view of a distal end of an ablation device according to a fourth embodiment of the present invention showing the ablation area in a non-deflected position;

FIG. 17 is a fragmented side sectional view of the distal end of the ablation device shown in FIG. 16;

FIGURE 18 is an end view of the ablation device of FIG. 16 shown in a deflected position; and FIG. 19 is a fragmented side sectional view of the device shown in FIG. 18;

FIG. 20 is a side view illustrating the positioning of the distal end of the ablation device shown in FIG. 1 in a body lumen with the ablation area at the distal end in a non-deflected position; and FIG. 21 is a side view illustrating the positioning of the distal end of the ablation device shown in FIG. 1 in a body lumen with the ablation area at the distal end in a deflected position.

DETAILED DESCRIPTION OF THE PRESENTLY PREFERRED EMBODIMENTS

Figure 1:
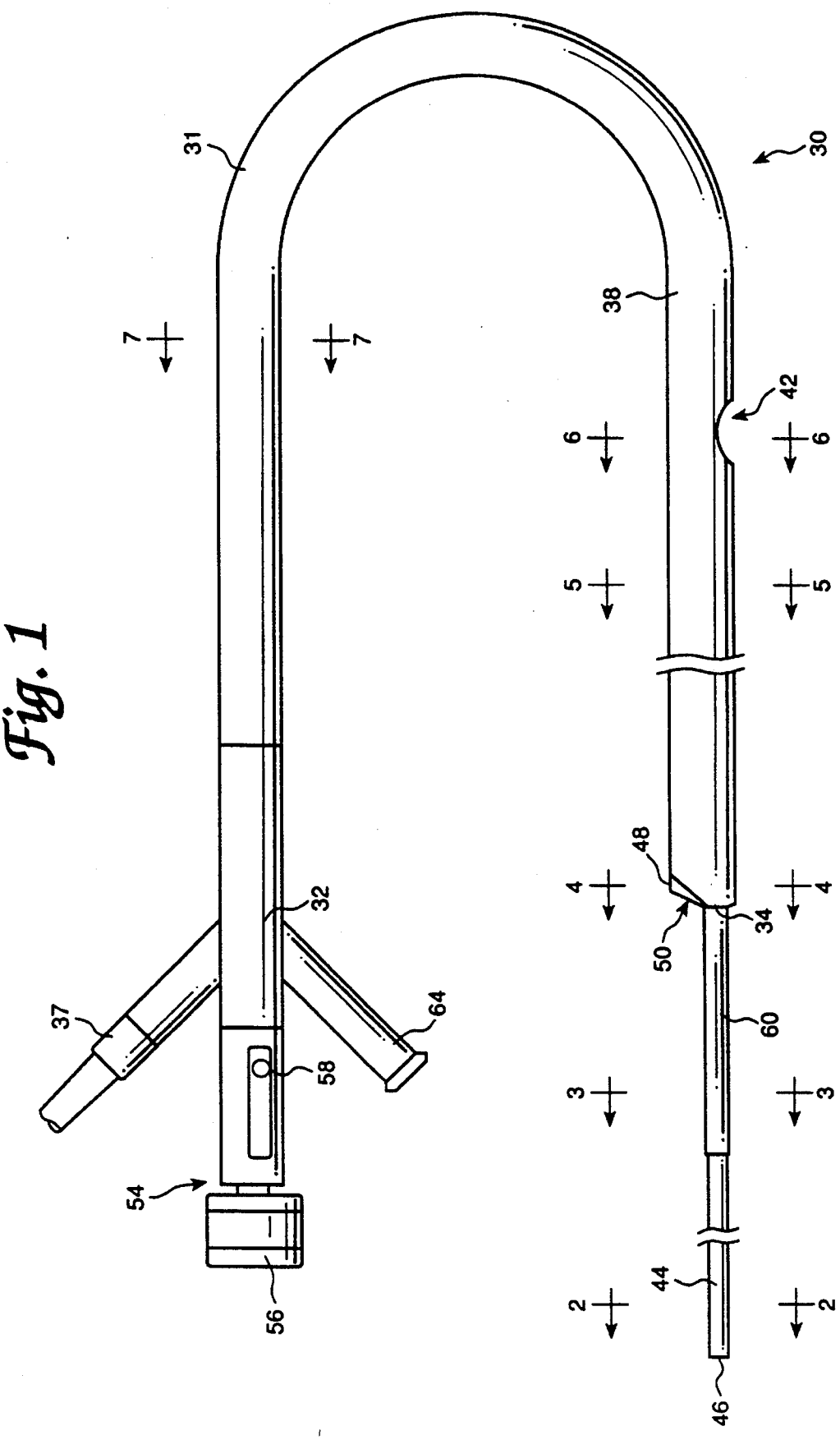
FIG. 1 is a side view of a first embodiment of an ablation device according to the principles of the present inventions.
Figure 2:
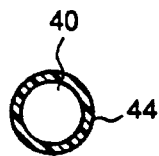
FIGS. 2–7 are cross-sectional views taken along lines 2—2, 3—3, 4—4, 5—5, 6—6 and 7—7 of FIG. 1.
Figure 3:
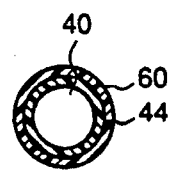

FIGS. 1–7 illustrate an apparatus for ablating biological tissue according to the principles of the present invention. The ablation device comprises a flexible catheter, generally indicated at 30, having a elongated body portion 31, a proximal end 32 and a distal end 34. Catheter 30 is sufficiently flexible so that at least a portion of catheter 30 can be inserted into a patient's vasculature system enabling distal end 34 to be positioned near an obstruction in a body cavity or lumen. Optical fibers 36 extend from proximal end 32 to distal end 34 for transmitting light energy from a light energy source (not shown) to distal end 34. Light energy is provided to a proximal end of optical fibers 36 through leg 37 at proximal end 32 of catheter 30. An outer jacket 38 surrounds the optical fibers thereby containing them in a single group. Outer jacket 38 is formed from a flexible material suitable for insertion into a human body. Preferably, outer jacket 38 is formed from a flexible plastic material such as polyurethane.

Figure 4:
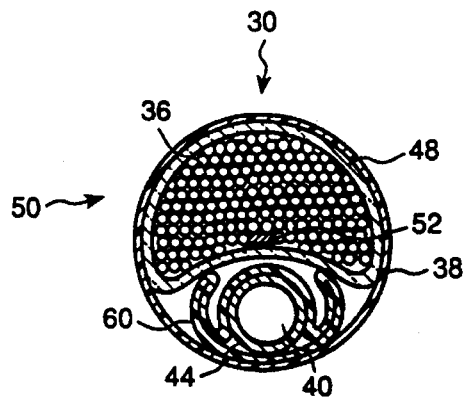
Figure 5:
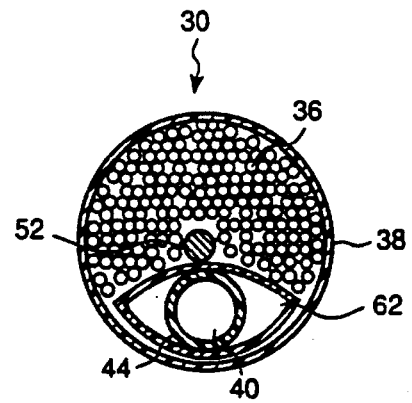
Figure 6:
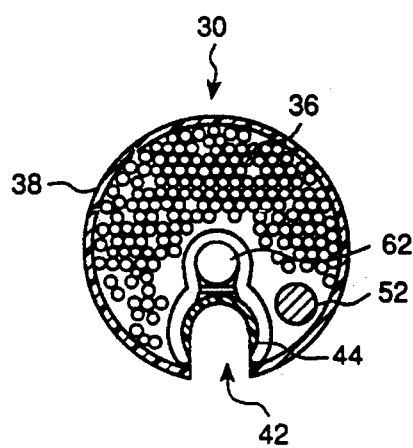
Figure 7:
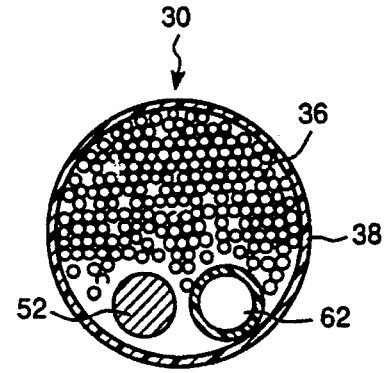

An inner member 44 extends through distal end 34 of catheter 30 and defines a guidewire lumen 40. Guidewire lumen 40 enables a guidewire (not shown) to pass through distal end 34 of catheter 30 for positioning distal end 34 at an obstruction in a body lumen. A guidewire proximal port 42, located a predetermined distance from distal end 34, provides a first access to guidewire lumen 40. An example of a catheter having a short guidewire lumen is disclosed in U.S. patent application No. 08/120,385, entitled "Fiber Optic Catheter with Shortened Guide Wire Lumen" which is incorporated herein by reference. It is to be understood, however, that the inner member and, thus, the guidewire lumen can extend the length of the catheter from proximal end 32 to distal end 34. In addition, the guidewire lumen can be eccentrically located, as shown in FIGS. 4–6, or axially located within catheter 30.

In a preferred embodiment of the present invention, inner member 44 extends beyond distal end 34. In addition, inner member 44 is eccentrically located with respect to the longitudinal axis of catheter 30. It is to be understood, however, that inner member 44 can extend along the longitudinal axis of catheter 30. A distal port for guidewire lumen 40 is provided at a distal end 46 of inner member 44. As a result, catheter 30 enables a guidewire to enter guidewire lumen 40 at proximal port 42 and exit therefrom at distal end 46.

In a preferred embodiment of the present invention, a radiopaque marker band 48 is located at distal end 34 of catheter 30. Radiopaque marker band 48 is made from a radiopaque material so that it can be viewed during surgery by X-ray or other conventional visualization techniques. Therefore, the surgeon can accurately manipulate catheter 30 through the venus system and position distal end 34 where desired by viewing the radiopaque band as the catheter passes through the vasculature. Radiopaque band 48 also enables the surgeon to view the movement of the ablation area during deflection. In a first embodiment of the present invention as shown in FIG. 4, radiopaque marker band 48 surrounds the distal end of a bundle of optical fibers 36 at distal end 34 of catheter 30.

The bundle of optical fibers 36 define an ablation area, generally indicated at 50, at distal end 34 of catheter 30. As discussed above, the ablation area 50 is where the biological tissue is ablated by light energy emitted from the distal end of optical fibers 36. The size of ablation area 50 corresponds to the cross-sectional area of the bundle of optical fibers 36 at distal end 34 of catheter 30. The density of light energy emitted from optical fibers 36 over the ablation area 50, which is referred to as the fluence, corresponds to the energy level of the light energy supplied to the proximal end of optical fibers 36 by a light energy source and the size of the ablation area 50. If both the energy level and the size of ablation area 50 remain constant during deflection, the energy density or fluence over the ablation also remains constant. If, however, the size of the ablation area increases and the energy level of the light energy supplied to the optical fibers remains constant during deflection, the energy density or fluence over the ablation area will decrease. Therefore, it is important to keep the size of ablation area 50 constant during deflection so that the fluence does not decrease.

Catheter 30 also includes a torque wire 52 extending from proximal end 32 to distal end 34. Torque wire 52 transmits rotational forces from a torque handle 56 on a torque device 54 to thereby rotate distal end 34 of catheter 30 for accurately positioning ablation area 50 where desired. More specifically, torque device 54 is a turn limiter device for transmitting a torque through torque wire 52 to thereby rotate distal end 34 of catheter 30. Examples of various types of turn limiter devices are disclosed in U.S. patent application No. 08/031,388, entitled "Turn Limiter for a Catheter with Twistable Tip", which is incorporated herein by reference. The turn limiter allows only a limited number of turns of torque handle 56 and includes an indicator 58 identifying the amount of turns provided by torque handle 56. In a preferred embodiment of the present invention, torque wire 52 decreases in diameter toward distal end 34 of catheter 30, has a rectangular shape at distal end 34, and is bonded to the optical fibers at distal end 34. It is to be understood, however, that the distal end of torque wire 52 can be bonded to other portions of catheter 30, such as radiopaque marker band 48. Examples of catheters having twistable distal ends that are capable of being rotated by a torque wire as described above are disclosed in U.S. patent application No. 08/031,391, now U.S. Pat. No. 5,352,197, entitled "Fiber Optic Catheter with Twistable Tip", which is incorporated herein by reference.

As discussed above, ablation area 50 is selectively deflectable away from guidewire lumen 40. In a first embodiment of the present invention, an inflatable balloon 60 is provided at distal end 34 of catheter for deflecting ablation area 50 from guidewire lumen 40. Balloon 60 is inflated by filling it with an inflation medium such as saline solution or other physiologically-acceptable material. The inflation medium is provided to balloon 60 through balloon lumen 62 extending through catheter 30 from proximal end 32. The inflation medium is introduced into balloon lumen 62 through leg 64 at proximal end 32.

According to a first embodiment of the present invention, as shown in FIG. 4, balloon 60 surrounds inner member 44 at distal end 34 of catheter 30. Balloon 60 is attached to the lower portion of inner member 44 so that during inflation balloon 60 forces ablation area 50 away from guidewire lumen 40. Also, in a preferred embodiment of the present invention, the material forming balloon 60 extends beyond distal end 34 of catheter 30. Balloon 60 is bonded to the entire periphery of inner member 44 beyond distal end 34 at a predetermined distance therefrom. In this embodiment of the present invention, the material forming balloon 60 is bonded to inner member 44 beyond distal end of catheter 30 such that a taper, increasing in a direction toward distal end 34 of catheter 30, is created when balloon 60 is inflated.

The deflection of ablation area 50 at distal end 34 of catheter 30 is discussed below with reference to FIGS. 8 and 9, which are views illustrating catheter 30 of FIGS. 1–7 showing ablation area 50 in a deflected position. More specifically, FIG. 9 is a cross-sectional view of catheter 30 taken along a line 9—9 of FIG. 8. Line 9—9 of FIG. 8 corresponds to line 4—4 of FIG. 1.

When balloon 60 is inflated, the bundle of optical fibers 36 at distal end 34 of catheter 30 is moved away from guidewire lumen 40 such that at least a portion of ablation area 50 is deflected outside an area defined by the cross-section area of catheter 30 at distal end 34. Thus, the size of the cut capable of being provided by the ablation area is increased. During deflection, ablation area 50 defined by the distal ends of optical fibers 36 remains constant. Therefore, the fluence or amount of light energy over the entire ablation area 50 at the distal end of the catheter remains constant. The use of a single ablation area 50 enables the smallest possible catheter to be provided for ablating an obstruction. Therefore, the catheter of the present invention is capable of being used in body lumens having a small diameter. Outer jacket 38 is sufficiently flexible such that when balloon 60 is inflated, outer jacket 38 stretches far enough to continue to surround optical fibers 36 as well as the other elements within catheter 30.

As discussed above, inflating of balloon 60 creates a taper 61, increasing in diameter toward distal end 34 of catheter 30, which assists in positioning ablation area 50 at the obstruction.

As shown in FIG. 9, the bundle of optical fibers 36 are deflected away from the guidewire lumen 40. Thus, the distance between the area of ablation and the guidewire can be increased while the catheter can continue to follow the path of the guidewire. Conventional laser catheters such as those disclosed in U.S. Pat. Nos. 5,188,672; 5,111,403; 5,029,588; and 4,966,596 deflect the ablation area, including the guidewire lumen, thereby working against the course of the guidewire. Therefore, it is not possible to increase the cutting area at the distal end of the catheter while still allowing the catheter to follow the guidewire.

Figure 10:
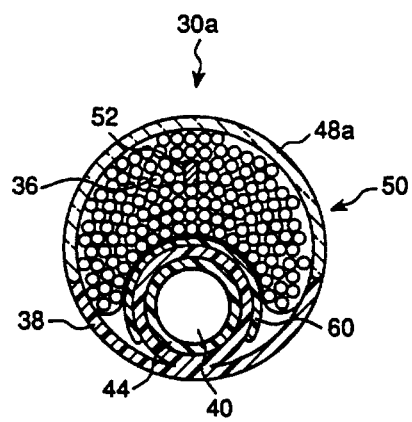
FIG. 10 is a cross-sectional view of a second embodiment for the distal end of the ablation device showing the ablation area in a non-deflected position.
Figure 11:
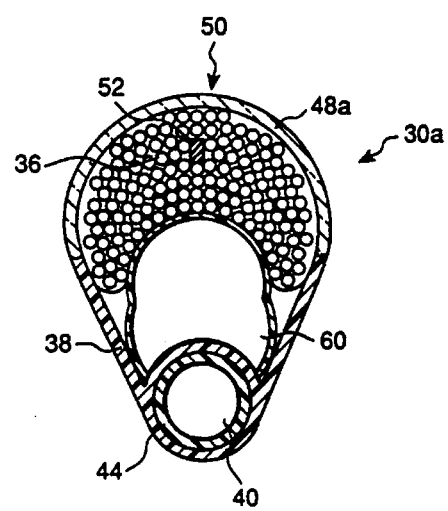
FIG. 11 is a cross-sectional view corresponding to the view shown in FIG. 10 showing the ablation area in a deflected position.
Figure 12:
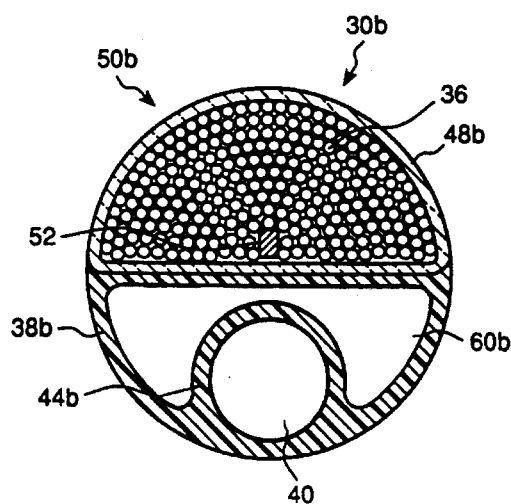
FIG. 12 is a cross-sectional view of a third embodiment for the distal end of the ablation device showing the ablation area in a non-deflected position.
Figure 13:
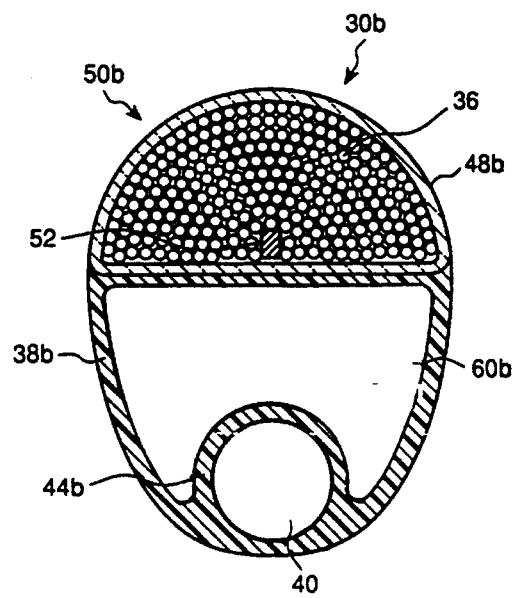
FIG. 13 is a cross-sectional view corresponding to the view shown in FIG. 12 showing the ablation area in a deflected position.

FIGS. 10 and 11 illustrate a second embodiment for the distal end of a balloon-type deflectable catheter 30*a* according to the principles of the present invention. In this embodiment, balloon 60 does not surround inner member 44. Instead, balloon 60 is positioned between inner member 44 and the bundle of optical fibers 36 defining ablation area 50. As in the previous embodiment, inflating balloon 60 shifts ablation area 50 away from inner member 44 and guidewire lumen 40 while the fluence over ablation area remains constant.

As in the previous embodiment, catheter 30*a* includes a torque wire 52. In this embodiment, however, radiopaque marker band 48*a* does not surround the distal end of the bundle of optical fibers 36. Instead radiopaque marker band 48*a* surrounds only the upper portion of the bundle of optical fibers 36.

FIGS. 12–15 illustrate a third embodiment of a balloon-type ablation device according to the principles of the present invention. In this embodiment, catheter 30*b* includes a lumen containing optical fibers 36, an inner member 44*b* defining guidewire lumen 40, and a balloon lumen 62*b*, all of which are formed from the same material and during a single extrusion.

An inflation area 60*b* in catheter 30*b* is formed by reshaping the material defining balloon lumen 62*b* at distal end 34*b*. This is accomplished, for example, by heating and pressurizing distal end 34*b* of catheter 30*b*. Inflation area 60*b* increases in size when inflation material is injected into balloon lumen 62*b*, thus deflecting ablation area 50*b* away from inner member 44*b*. As shown in FIG. 15, inflation area 60*b* extends beyond distal end 34*b* of catheter 30*b*. As a result, a taper 61*b* is created when inflation area 60*b* is inflated, which facilitates positioning of ablation area 50*b* at the desired location.

As in the embodiments of the present invention discussed above, catheter 30b includes a torque wire 52. In addition, catheter 30b includes a radiopaque marker band 48b surrounding the group of optical fibers 36 at distal end 34b of catheter 30b.

FIGS. 16–19 illustrate a second embodiment of the ablation device according to the principles of the present invention. In this embodiment, catheter 30c includes a mechanical hinge assembly, generally indicated at 80, near distal end 34c for deflecting the distal ends of all of the optical fibers 36. Hinge assembly 80 moves between a closed or non-extended position, shown in FIGS. 16 and 17, and an open or extended position, shown in FIGS. 18 and 19, thereby deflecting ablation area 50c. Actuating hinge assembly 80 is accomplished by applying a tensile force on a pullwire 82, which is attached to a central pivot 84 in hinge assembly 80. As in the previous embodiment, outer jacket 38c surrounds the internal structures of the catheter.

Hinge assembly 80 includes a first hinge member 86 pivotally attached at a first end to a bundle of optical fibers 36 and a second hinge member 88 pivotally attached at a first end to inner member 44c. The first and second hinge members 86 and 88 are pivotally attached to one another at second ends thereof at central pivot 84. A pivot pin 90 extends between the ends of the first and second hinge members 86 and 88 at central pivot 84.

FIGS. 20 and 21 illustrate a method for using the catheters of the present invention to ablate an occlusion in a body lumen by deflecting the ablation area as discussed above. FIGS. 20 and 21 use catheter 30 of FIG. 1 merely as an example. Catheter 30 is inserted into a body lumen 100 until distal end 34 of catheter 30 is near an obstruction 102. Radiopaque marker 48 enables the surgeon to visualize the distal end of catheter 30 during insertion to accurately position distal end 34 at obstruction 102. Guidewire 104 assists in positioning distal end 34 of catheter 30 at the obstruction by enabling catheter 30 to pass over guidewire 104 by sliding inner member 44 and catheter 30 over guidewire 104.

Once catheter 30 is positioned near obstruction 102, light energy is provided to the proximal end of the optical fibers, which transmit the light energy through catheter 30 to distal end 34. The light energy 106 emitted from the distal end of the optical fiber ablates obstruction 102. Rotating distal end 34 of catheter 30 increases the size of the cut produced by light energy 106 emitted from ablation area 50 in a concentric direction. To increase the size of the cut in a radial direction with respect to the longitudinal axis of catheter 30, ablation area 50 is deflected as shown in FIG. 21. Thus, light energy 106 no longer extends distal end 34 parallel to the longitudinal axis of catheter 30, but, instead, is emitted from distal end 34 of catheter 30 at an angle with respect to the longitudinal axis thereof. In this manner, a larger cutting area can be provided from catheter 30 without decreasing the fluence of the light energy emitted from distal end 34 of catheter 30. Catheter 30 can also be rotated and/or manipulated while ablation area 50 is deflected so that the size of the cut provided by light energy 106 is increased and more accurate control of the catheter is possible. Catheter 30 can continue to be inserted over guidewire 104 even when in a deflected position as shown in FIG. 21, thus improving the performance of the catheter for ablating obstructions in body lumens.

It is to be understood that the amount by with the ablation area is deflected can be controlled by limiting the amount of inflation material injected into the balloon lumen, in the case of the first three embodiments described above, or limiting the distance the pullwire is actuated, in the case of the fourth embodiment described above. Also, repeated passes of the distal end of the catheter over the obstruction can be performed by removing the distal end of the catheter from beyond the obstruction and again moving the distal end of the catheter through the obstruction. If necessary, the balloon can be deflated or the pullwire released to return the distal end of the catheter to its original position for removing the distal end of the catheter from beyond the obstruction.

It will, thus, be understood that the objects of this invention have been fully and effectively accomplished. It should be appreciated, however, that the foregoing preferred specific embodiments have been shown and described for the purposes of the invention and are subject to change without departure from such principles. Therefore, this invention includes all modifications encompassed within the spirit and scope of the following claims.

What is claimed is:

1. An apparatus for ablating biological tissue having a deflectable ablation area, comprising:
   an elongated catheter having a distal end, a proximal end, an elongated body portion, and a first cross-sectional area at said distal end when said catheter is in an undeflected state including;
   a sheath,
   a plurality of optical fibers located within said sheath and extending between said proximal end and said distal end of said catheter, each optical fiber in said plurality of optical fibers having distal end and an end surface at said distal end, wherein an ablation area is located at said distal end of said elongated catheter, said ablation area being defined by a closed figure that encompasses said end surfaces of all of said optical fibers, said optical fibers generally pointing in an axial direction of said elongated catheter when said catheter is in said undeflected state, and
   deflecting means for selectively deflecting all of said optical fibers generally away from said axial direction of said elongated catheter such that at least a portion of said ablation area extends beyond said first cross-sectional area of said catheter and such that an amount of light energy over said entire ablation area remains constant whether or not said deflecting means is actuated, said deflecting means being contained within said sheath.

2. An apparatus as defined in claim 1, wherein said deflecting means comprises an inflatable balloon positioned within said catheter at said distal end thereof.

3. An apparatus as defined in claim 1, wherein said catheter further comprises a rotating means for rotating said distal end of said catheter.

4. An apparatus as defined in claim 1, further comprising an extended inner member extending beyond said distal end of said catheter and a guidewire lumen extending through said inner member.

5. An apparatus as defined in claim 1, wherein said elongated catheter body includes a guidewire lumen port located a predetermined distance from said distal end of said catheter.

6. An apparatus as defined in claim 1, wherein said deflecting means comprises a mechanical hinge assembly selectively movable between an extended position and a non-extended position such that said ablation area is deflected when said hinge assembly is in said extended position.

7. An apparatus as defined in claim 1, wherein said sheath comprising a flexible outer jacket, said outer jacket stretching when said deflecting means is actuated thereby completely encompassing said optical fibers even when said deflecting means is actuated.

8. An apparatus as defined in claim 1, wherein actuation of said deflecting means also causes a taper in said catheter that increases in diameter in a direction toward said distal end said catheter.

9. An apparatus as defined in claim 1 further comprising:

an inner member extending through at least said distal end of said catheter, wherein said deflecting means shifts said optical fibers relative to said inner member.

10. An apparatus as defined in claim 9, wherein said deflecting means comprises:

an inflatable balloon positioned within said catheter between said distal ends of said optical fibers and said inner member; and a balloon lumen extending through said catheter from said proximal end to said balloon for providing an inflation medium to said balloon.

11. An apparatus as defined in claim 10, wherein said catheter further comprises a rotating means for rotating said distal end of said catheter.

12. An apparatus as defined in claim 11, wherein said inner member is eccentrically located within said catheter.

13. An apparatus as defined in claim 12, wherein said catheter includes a radiopaque marker provided at said distal end of said catheter.

14. An apparatus as defined in claim 13, wherein said rotating means comprises:

a torque wire extending through said catheter; and a turn limiter assembly for imparting a torque in said torque wire.

15. A method for ablating an obstruction comprising the steps of:

positioning a distal end of a catheter near said obstruction, said catheter including a sheath encompassing a portion of said catheter and a plurality of optical fibers extending from a proximal end to said distal end of said catheter, each optical fiber in said plurality of optical fibers having a distal end and an end surface at said distal end, wherein an ablation area is located at said distal end of said catheter, said ablation area being defined by a closed figure that encompasses said end surfaces of all of said optical fibers, said optical fibers generally pointing in an axial direction of said elongated catheter when in an undeflected state, and said catheter having a first cross-sectional area when in said undeflected state; and deflecting said optical fibers generally away from said axial direction of said elongated catheter via a deflecting device contained within said sheath such that at least a portion of said ablation area extends beyond an area defined by said first cross-sectional area of said catheter and such that an amount of light energy over said entire ablation area remains constant whether or not said optical fibers are deflected.

16. A method for ablating an obstruction as defined in claim 15, wherein said deflecting step comprises the step of inflating a balloon positioned within said catheter, said balloon being positioned between an inner member extending through at least said distal end of said catheter and said ablation area such that said ablation area is moved away from said said inner member.

17. A method for ablating an obstruction as defined in claim 16, further comprising the step of:

rotating said distal end of said catheter by providing a torque to a torque wire extending through said catheter from said proximal end to said distal end thereof.

18. A method for ablating an obstruction as defined in claim 15, wherein said deflecting step includes the step of actuating a mechanical hinge assembly located adjacent said ablation area at said distal end of said catheter such that said ablation area is moved away from an inner member extending through at least said distal end of said catheter.

19. A method for ablating an obstruction as defined in claim 18, wherein said mechanical hinge includes a first hinge member pivotally attached at a first end to a bundle of optical fibers forming said ablation area and a second hinge member pivotally attached at a first end to a portion of said catheter, said first and second hinge member being pivotally attached to one another at second ends thereof, wherein said actuating step includes the step of applying a tensile force on a pullwire connected to said pivotable connection between said first and second hinge members.

* * * * *